(12) United States Patent
Lal et al.

(10) Patent No.: US 6,858,227 B1
(45) Date of Patent: Feb. 22, 2005

(54) VITAMIN E CONJUGATES

(75) Inventors: Manjari Lal, Bellevue, WA (US);
Yuehua Zhang, Mill Creek, WA (US);
Nagesh Palepu, Mill Creek, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 0 days.

(21) Appl. No.: 10/300,678

(22) Filed: Nov. 20, 2002

Related U.S. Application Data
(60) Provisional application No. 60/332,035, filed on Nov. 21, 2001.

(51) Int. Cl.[7] .................... A61K 9/08; A61K 9/107; A61K 9/127; A61K 31/4015; C07D 407/12
(52) U.S. Cl. .................... 424/450; 424/455; 514/422; 514/424; 548/525; 548/543
(58) Field of Search .................... 548/525–543; 424/450, 455; 514/422, 424

(56) References Cited

U.S. PATENT DOCUMENTS

| | | | |
|---|---|---|---|
| 4,665,204 A | 5/1987 | Wirth | |
| 5,606,080 A | 2/1997 | Ogata et al. | |
| 5,610,180 A | 3/1997 | Fariss | |
| 5,858,398 A | 1/1999 | Cho | |
| 5,945,409 A | * 8/1999 | Crandall | |
| 6,319,943 B1 | 11/2001 | Joshi et al. | |
| 6,387,882 B1 | 5/2002 | Ogata et al. | |
| 6,479,540 B1 | 11/2002 | Constantinides et al. | |

FOREIGN PATENT DOCUMENTS

| | | |
|---|---|---|
| WO | WO 95/11039 | 4/1995 |
| WO | WO 95/31217 | 11/1995 |
| WO | WO 98/30205 | 7/1998 |
| WO | WO 99/04787 | 2/1999 |
| WO | WO 00/71163 | 11/2000 |
| WO | 0071163 | * 11/2000 |
| WO | WO 01/229373 | 4/2001 |

* cited by examiner

*Primary Examiner*—Rita Desai
(74) *Attorney, Agent, or Firm*—Christensen O'Connor Johnson Kindness PLLC

(57) ABSTRACT

Vitamin E conjugates, methods for their preparation, and compositions that include the conjugates. The vitamin E conjugates include a tocopherol moiety covalently coupled through a linker moiety to either a pyroglutamate moiety, a pyrrolidinone moiety, or a gentisic acid moiety.

21 Claims, 8 Drawing Sheets

R1 =

R1 =

R1 =

VITAMIN E CONJUGATES

CROSS-REFERENCE TO RELATED APPLICATION

This application claims the benefit of U.S. Provisional Application No. 60/332,035, filed Nov. 21, 2001, incorporated herein by reference in its entirety.

FIELD OF THE INVENTION

The present invention relates to vitamin E conjugates that are useful in solubilizing lipophilic and relatively water-insoluble compounds.

BACKGROUND OF THE INVENTION

Hundreds of medically useful compounds are discovered each year, but clinical use of these drugs is possible only if a drug delivery vehicle is developed to transport them to their therapeutic target in the human body. This problem is particularly critical for drugs requiring intravenous injection in order to reach their therapeutic target or dosage, but which are water insoluble or poorly water soluble. For such hydrophobic compounds, direct injection may be impossible or highly dangerous, and can result in hemolysis, phlebitis, hypersensitivity, organ failure, and/or death. Such compounds are termed by pharmacists "lipophilic", "hydrophobic", or, in their most difficult form, "amphiphobic".

A few examples of therapeutic substances in these categories are ibuprofen, diazepam, griseofulvin, cyclosporin, cortisone, proleukin, etoposide and paclitaxel. Kagkadis, K. A., et al., *PDA J Pharm Sci Tech* 50(5):317–323, 1996; Dardel, O., *Anaesth Scand* 20:221–24, 1976; Sweetana, S. and M. J. U. Akers, *PDA J Pharm Sci Tech* 50(5):330–342, 1996.

Administration of chemotherapeutic or anti-cancer agents is particularly problematic. Low solubility anti-cancer agents are difficult to solubilize and supply at therapeutically useful levels. On the other hand, water-soluble anti-cancer agents are generally taken up by both cancer and non-cancer cells thereby exhibiting non-specificity.

Efforts to improve water-solubility and comfort of administration of such agents have not solved, and may have worsened, the two fundamental problems of cancer chemotherapy: (1) non-specific toxicity and (2) rapid clearance form the bloodstream by non-specific mechanisms. In the case of cytotoxins, which form the majority of currently available chemotherapies, these two problems are clearly related. Whenever the therapeutic is taken up by noncancerous cells, a diminished amount of the drug remains available to treat the cancer, and more importantly, the normal cell ingesting the drug is killed.

To be effective in treating cancer, the chemotherapeutic must be present throughout the affected tissue(s) at high concentration for a sustained period of time so that it may be taken up by the cancer cells, but not at so high a concentration that normal cells are injured beyond repair. Obviously, water soluble molecules can be administered in this way, but only by slow, continuous infusion and monitoring, aspects which entail great difficulty, expense and inconvenience.

A more effective method of administering a cancer therapeutic, particularly a cytotoxin, is in the form of a dispersion of oil in which the drug is dissolved. These oily particles are made electrically neutral and coated in such a way that they do not interact with plasma proteins and are not trapped by the reticuloendothelial system (RES), instead remaining intact in the tissue or blood for hours, days, or even weeks. In most cases, it is desirable if the particles also distribute themselves into the surrounding lymph nodes which are injected at the site of a cancer. Nakamoto, Y., et al., *Chem Pharm Bull* 23(10):2232–2238, 1975; Takahashi, T., et al., *Tohoku J Exp Med* 123:235–246, 1977. In many cases direct injection into blood is the route of choice for administration. Even more preferable, following intravenous injection, the blood-borne particles may be preferentially captured and ingested by the cancer cells themselves. An added advantage of a particulate emulsion for the delivery of a chemotherapeutic is the widespread property of surfactants used in emulsions to overcome multidrug resistance.

For drugs that cannot be formulated as an aqueous solution, emulsions have typically been most cost-effective and gentle to administer, although there have been serious problems with making them sterile and endotoxin free so that they may be administered by intravenous injection. The oils typically used for pharmaceutical emulsions include saponifiable oils from the family of triglycerides, for example, soybean oil, sesame seed oil, cottonseed oil, safflower oil, and the like. Hansrani, P. K., et al., *J Parenter Sci Technol* 37:145–150, 1983. One or more surfactants are used to stabilize the emulsion, and excipients are added to render the emulsion more biocompatible, stable and less toxic. Lecithin from egg yolks or soybeans is a commonly used surfactant. Sterile manufacturing can be accomplished by absolute sterilization of all the components before manufacture, followed by absolutely aseptic technique in all stages of manufacture. However, improved ease of manufacture and assurance of sterility is obtained by terminal sterilization following sanitary manufacture, either by heat or by filtration. Unfortunately, not all emulsions are suitable for heat or filtration treatments.

Stability has been shown to be influenced by the size and homogeneity of the emulsion. The preferred emulsion consists of a suspension of sub-micron particles, with a mean size of no greater than 200 nanometers. A stable dispersion in this size range is not easily achieved, but has the benefit that it is expected to circulate longer in the bloodstream. Furthermore, less of the stable dispersion is phagocytized non-specifically by the reticuloendothelial system. As a result the drug is more likely to reach its therapeutic target. Thus, a preferred drug emulsion will be designed to be actively taken up by the target cell or organ, and is targeted away from the RES.

The use of vitamin E in emulsions is known. In addition to the hundreds of examples where vitamin E in small quantities, for example, less than 1% (see, for example, R. T. Lyons, "Formulation development of an injectable oil-in-water emulsion containing the lipophilic antioxidants α-tocopherol and β-carotene," *Pharm Res* 13(9):S-226, 1996) as an anti-oxidant in emulsions, the first primitive, injectable vitamin E emulsions per se were made by Hidiroglou for dietary supplementation in sheep and for research on the pharmacokinetics of vitamin E and its derivatives. Hidiroglou M. and K. Karpinski, *Brit J Nutrit* 59:509–518, 1988.

For mice, an injectable form of vitamin E was prepared by Kato and coworkers. Kato Y., et al., *Chem Pharm Bull* 41(3):599–604, 1993. Micellar solutions were formulated with Tween 80, Brij 58, and HCO-60. Isopropanol was used as a co-solvent, and was then removed by vacuum evaporation; the residual oil glass was then taken up in water with vortexing as a micellar suspension. An emulsion was also prepared by dissolving vitamin E with soy phosphatidycholine (lecithin) and soybean oil. Water was added and the emulsion prepared with sonication.

In 1983, E-Ferol, a vitamin E emulsion was introduced for vitamin E supplementation and therapy in neonates. Alade, S. L., et al., *Pediatrics* 77(4):593–597, 1986. Within a few months over 30 babies had died as a result of receiving the product, and the product was promptly withdrawn by FDA order. The surfactant mixture used in E-Ferol to emulsify 25 mg/mL vitamin E consisted of 9% Tween 80 and 1% Tween 20. These surfactants seem ultimately to have been responsible for the unfortunate deaths. This experience illustrates the need for improved formulations and the importance of selecting suitable biocompatible surfactants and carefully monitoring their levels in parenteral emulsions.

An alternative means of solubilizing low solubility compounds is direct solubilization in a non-aqueous milieu, for example, alcohol (such as ethanol), dimethylsulfoxide, or triacetin. An example in PCT application WO 95/11039 describes the use of vitamin E and the vitamin E derivative TPGS in combination with ethanol and the immunosuppressant molecule cyclosporin. Alcohol-containing solutions can be administered with care, but are typically given by intravenous drip to avoid the pain, vascular irritation, and toxicity associated with bolus injection of these solutions.

Problems with pharmaceutical formulations in non-aqueous solvents and solubilizers such as alcohol (ethanol, isopropanol, benzyl alcohol) relate to the ability of these solvents to extract toxic substances, for example, plasticizers from their containers. The current commercial formulation for the anti-cancer drug paclitaxel, for example, consists of a mixture of hydroxylated castor oil and ethanol, and rapidly extracts plasticizers such as di(2-ethylhexyl)phthalate from commonly used intravenous infusion tubing and bags. Adverse reactions to the plasticizers have been reported, such as respiratory distress, necessitating the use of special infusion systems at extra expense and time. Waugh,et al., *Am J Hosp Pharmacists* 48:1520, 1991.

In light of these problems, it can be seen that the ideal emulsion vehicle would be inexpensive, non-irritating or even nutritive, and palliative in itself, terminally sterilizable by either heat or filtration, stable for at least 1 year under controlled storage conditions, accommodate a wide variety of water insoluble and poorly soluble drugs and be substantially ethanol-free. In addition to those drugs that are lipophilic and dissolve in oils, also needed is a vehicle that will stabilize, and carry in the form of an emulsion, drugs which are poorly soluble in lipids and in water.

The present invention seeks to fulfill these needs and provides further related advantages.

SUMMARY OF THE INVENTION

The present invention provides vitamin E conjugates, methods for their preparation, and compositions that include the conjugates.

In one aspect, the invention provides vitamin E conjugates. The vitamin E conjugates include conjugates of vitamin E, vitamin E succinate, and vitamin E polyethylene glycol amine with pyroglutamic acid, pyrrolidinone, and gentisic acid. The vitamin E conjugates of the invention have improved solubilizing effects in the delivery of lipophilic and relatively water-insoluble compounds, such as therapeutic drugs and cosmetics.

The vitamin E conjugates of the invention include a tocopherol moiety covalently coupled through a linker moiety to either a pyroglutamate moiety, a pyrrolidinone moiety, or a gentisic acid moiety. The linker moiety can include an amine group or a dicarboxylic acid diester group. In one embodiment, the linker moiety includes a succinic acid diester group. In another embodiment, the linker moiety includes a polyoxyethylene group. In a further embodiment, the linker moiety comprises a bispropylamino polyoxyethylene group.

In another aspect of the invention, methods for making the vitamin E conjugates are provided.

In a further aspect, compositions that include the vitamin E conjugates are provided. In one embodiment, the composition is a true solution. In another embodiment, the composition is an emulsion.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
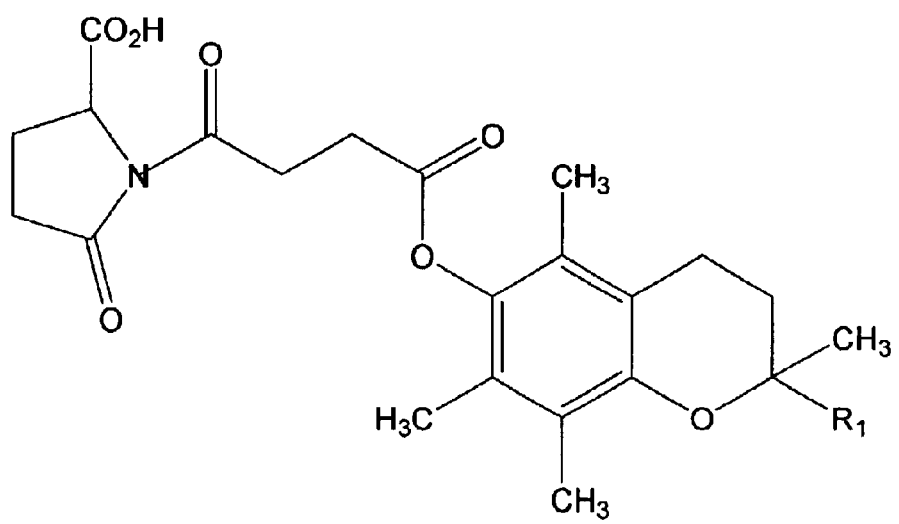
FIG. 1 illustrates the chemical structure of a representative vitamin E pyroglutamate conjugate of the invention.
Figure 1:
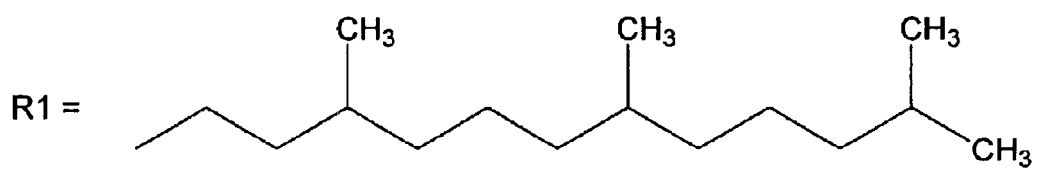

The present invention provides vitamin E conjugates, methods for their preparation, and compositions that include the vitamin E conjugates. The vitamin E conjugates include conjugates of vitamin E, vitamin E succinate, and vitamin E polyethylene glycol amine with pyroglutamic acid, pyrrolidinone, and gentisic acid. The vitamin E conjugates of the invention have improved solubilizing effects in the delivery of lipophilic and relatively water-insoluble compounds, such as therapeutic agents and cosmetic agents.

As used herein, the term "vitamin E" refers to a compound that is a member of the tocopherol family. Tocopherols are a family of natural and synthetic compounds, also known by the generic names tocols or vitamin E. The most abundant tocopherol is α-tocopherol. Other members of this family class include α-, β-, γ-, and δ-tocotrienols. Tocopherols also include α-tocopherol derivatives, such as tocopherol acetate, phosphate, succinate, nicotinate, and linoleate.

The term "conjugate" refers to a chemical compound. The vitamin E conjugates of the invention are compounds that include a vitamin E moiety and, therefore, are derivatives of vitamin E.

Examples of lipophilic therapeutic agents that may be advantageously solubilized by the vitamin E conjugates of the invention include analgesics, anti-inflammatory agents, anthelmintics, anti-arrhythmic agents, antibiotics, anticoagulants, antidepressants, antidiabetics, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympthomimetics, parathyroid calcitonin, prostaglandins, radio-pharmaceuticals, sex hormones, anti-allergic agents, stimulants, anoretics, sympthomimetics, thyroid agents, vasodilators, and xanthines. Some examples of lipophilic drugs that may be advantageously solubilized by the vitamin E conjugates of the invention include taxanes (e.g., paclitaxel), etoposide, camptothecin, tacrolimus, teniposide, lorazepam, and steroids (e.g., testosterone, betamethasone, and their derivatives).

Examples of relatively water-insoluble therapeutic drugs that may be advantageously solubilized by the vitamin E conjugates of the invention include immunosuppressive agents, such as cyclosporins, cyclosporin A; immunoactive agents; antiviral and antifungal agents, such as itraconazole; antineoplastic agents; analgesics; anti-inflammatory agents; antibiotics; anti-epileptics; anesthetics; hypnotics; sedatives; antipsychotic agents; neuroleptic agents; antidepressants; anxiolytics; anticonvulsant agents; antimuscarinic and muscarinic agents; antiadrenergic and antiarrhythmic agents; antihypertensive agents; antineoplastic agents; hormones; and nutrients. A detailed description of these and other suitable drugs may be found in Remington's Pharmaceutical Sciences, 19$^{th}$ ed., Mack Publishing Co., Philadelphia, Pa., 1990.

In one aspect of the invention, vitamin E conjugates are provided.

Figure 2:
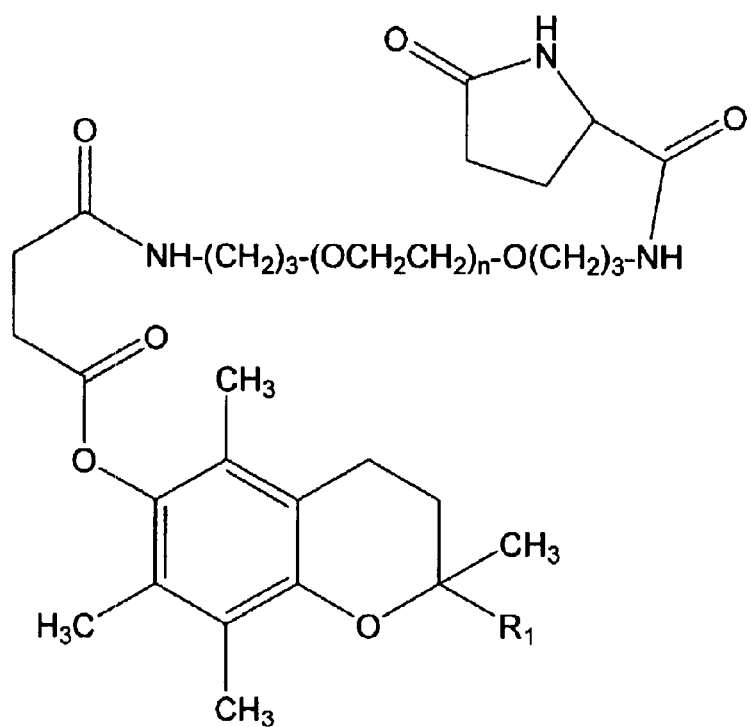
FIG. 2 illustrates the chemical structure of a representative vitamin E pyroglutamate conjugate of the invention.
Figure 2:
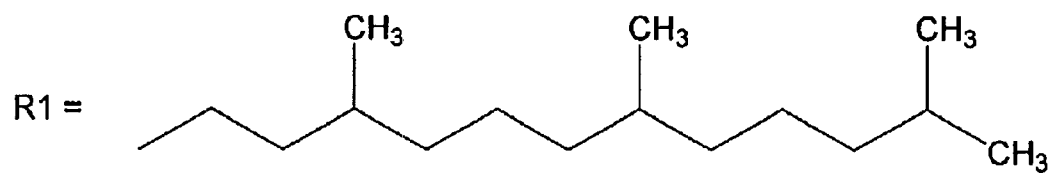
Figure 3:
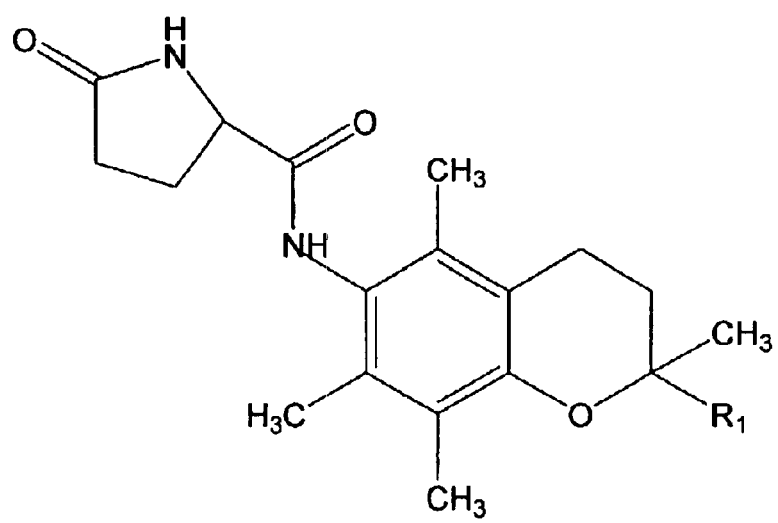
FIG. 3 illustrates the chemical structure of a representative vitamin E pyroglutamate conjugate of the invention.
Figure 3:
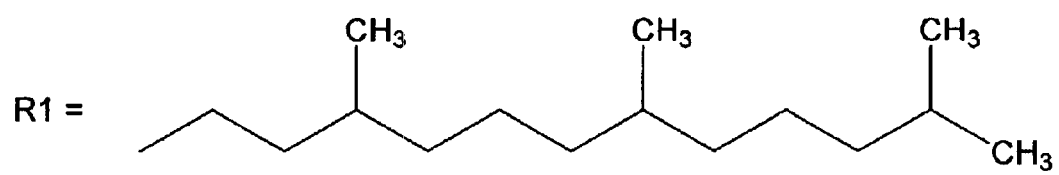

The invention provides vitamin E pyroglutamic acid (pyroglutamate) conjugates. In one embodiment, the present invention provides a vitamin E succinic acid (VESA) pyroglutamate conjugate. The structure of a representative conjugate is shown in FIG. 1. The preparation of the conjugate is described in Example 1. In another embodiment, the present invention provides a vitamin E succinic acid (VESA) polyethylene glycol amine pyroglutamate conjugate. The structure of a representative conjugate is shown in FIG. 2. The preparation of the conjugate is described in Example 2. For this conjugate, n=15–20. In another embodiment, the present invention provides a vitamin E amine pyroglutamate conjugate. The structure of a representative conjugate is shown in FIG. 3. The preparation of the conjugate is described in Example 3.

Figure 4:
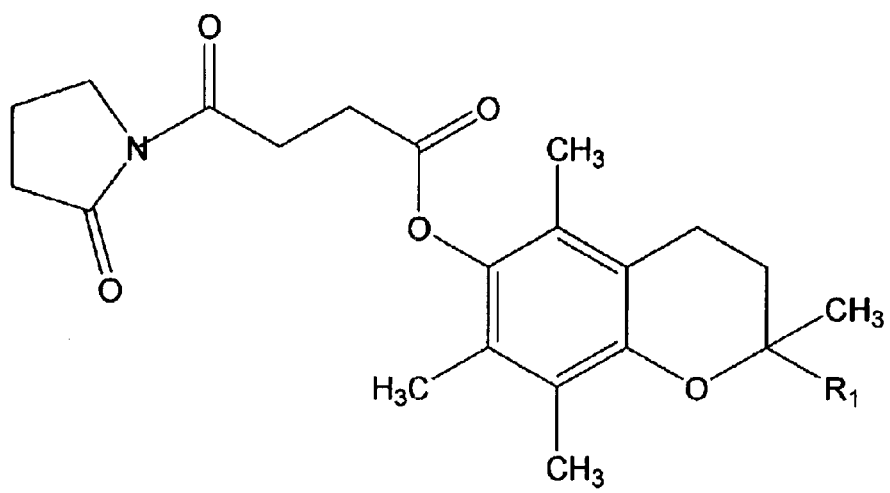
FIG. 4 illustrates the chemical structure of a representative vitamin E pyrrolidinone conjugate of the invention.
Figure 4:
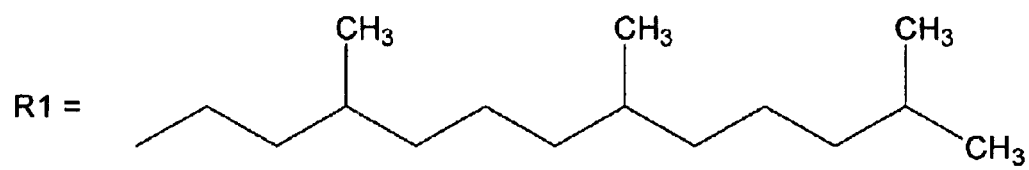

The invention provides vitamin E pyrrolidinone conjugates. In one embodiment, a vitamin E succinic acid (VESA) pyrrolidinone conjugate is provided. The structure of a representative conjugate is shown in FIG. 4. The preparation of the conjugate is described in Example 4.

Figure 5:
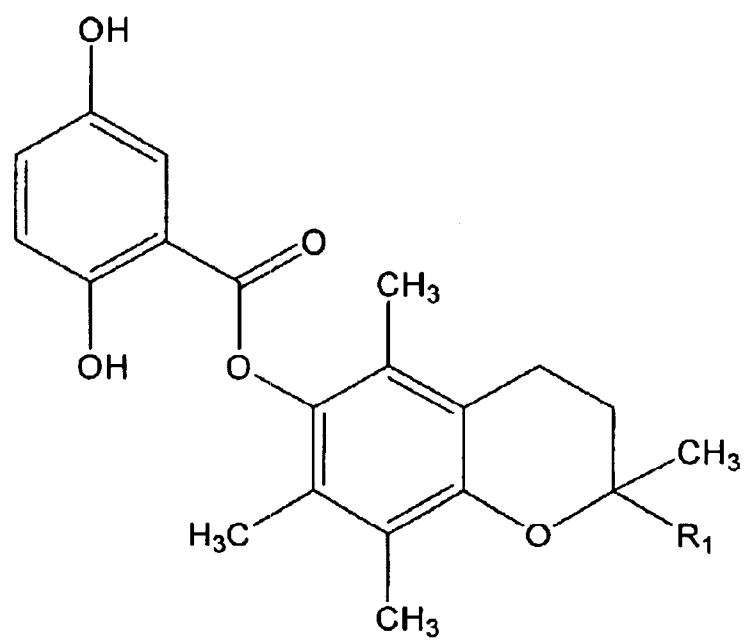
FIG. 5 illustrates the chemical structure of a representative vitamin E gentisic acid conjugate of the invention.
Figure 5:
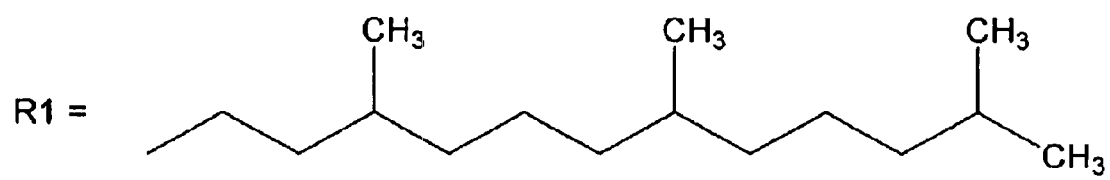

The invention provides vitamin E gentisic acid conjugates. In one embodiment, a vitamin E gentisic acid conjugate is provided having the structure shown in FIG. 5. The preparation of the conjugate is described in Example 5.

The vitamin E conjugates of the invention can be advantageously combined with a one or more lipophilic or relatively water-insoluble compounds to solubilize the compound to provide a composition. Representative compositions include true solutions (i.e., all components in a single phase) and emulsions (e.g., oil-in-water and water-in-oil emulsions).

As used herein, the term "emulsion" refers to a colloidal dispersion of two immiscible liquids in the form of droplets, whose diameter, in general, are between 0.1 and 3.0 microns. An emulsion is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as oil and water, stabilized by an interfacial film of surfactant molecules. A microemulsion has a mean droplet diameter of less than about 200 nm, typically between from about 10 to about 50 nm.

In another aspect, the invention provides compositions that include a vitamin E conjugate. Representative compositions include solutions and emulsions.

In one embodiment, the composition is a solution in which the vitamin E conjugate is combined with a lipophilic or relatively water-insoluble therapeutic or cosmetic agent. In such a composition, the therapeutic or cosmetic agent and the vitamin E conjugate are in solution. Alternatively, the therapeutic or cosmetic agent and the vitamin E conjugate can be combined with a solvent to provide a solution. Suitable solvents include those commonly used in the pharmaceutical and cosmetic compositions, for example, those noted in Remington's Pharmaceutical Sciences, 19$^{th}$ ed., Mack Publishing Co., Philadelphia, Pa., 1990. Suitable solvents include alcohols, such as polyethylene glycol (e.g., PEG 200, PEG 300, and PEG 400), propylene glycol, and ethanol, among others. Other useful solvents include those described in U.S. Pat. No. 6,458,373, incorporated herein by reference in its entirety.

In another embodiment, the composition is an emulsion in which the vitamin E conjugate and a lipophilic or relatively water-insoluble therapeutic or cosmetic agent is combined with water. In such a composition, the therapeutic or cosmetic agent and the vitamin E conjugate are present in a phase (e.g., oil phase) that is dispersed in another phase (e.g., water phase). While these compositions are referred to as emulsions, it will be understood that the compositions can be considered to be micellar solutions, microemulsions, vesicular suspensions, or mixtures of one or more of these physical states. The emulsions that include the vitamin E conjugates can also include solvents, such as described above, and other materials commonly found in emulsions including, for example, surfactants. Suitable surfactants include surfactants manufactured by chemical processes or purified from natural sources or processes, and can be anionic, cationic, nonionic, and zwitterionic. Useful surfactants are described in Becher, P., *Emulsions: Theory and Practice*, Robert E. Krieger Publishing, Malabar, Fla., 1965; *Pharmaceutical Dosage Forms: Dispersed Systems*, Vol. I, Surfactants, Martin M. Rigear; U.S. Pat. No. 5,955,723; and U.S. Pat. No. 6,458,373, each incorporated herein by reference in its entirety.

The following examples are provided for the purpose of illustrating, not limiting, the present invention.

EXAMPLES

Example 1

The Preparation of a Representative Vitamin E Succinic Acid Pyroglutamate Conjugate In this example, the preparation of a representative vitamin E pyroglutamate conjugate is described.

To 10 g vitamin E succinic acid (VESA) (Aldrich or Eastman) in 150 ml tetrahydrofuran (THF) was added 2.85 g N-methylmorpholine dropwise while stirring and maintaining the temperature at 0° C. with an ice water salt bath. This was followed by dropwise addition of 3.34 g isobutyl chloroformate in THF over a period of 15 minutes while continued stirring at 0° C. The reaction mixture was then removed from the ice bath and left stirring at room temperature for 30 minutes. After an additional hour of stirring, the solution was then filtered using Celite on a glass filter to remove the chloride salt of N-methylmorpholine. The resulting solution was added dropwise to a mixture 2.92 g L-pyroglutamic acid dissolved in 30 ml hot water containing 0.5 ml N,N-dimethylformamide (DMF) and 2.85 g triethylamine. The temperature on addition was maintained at 0° C. The solution was left stirring at room temperature overnight. The following day, the solution was concentrated to dryness under reduced pressure to yield a gelatinous product. The product was then dissolved in 250 ml dichloromethane and extracted with 3×250 ml 0.1 N HCl, washed with saturated $NaHCO_3$ followed by 200 ml saturated NaCl solution, and dried over $MgSO_4$. The $MgSO_4$ was filtered with Whatman #1 filter and the filtrate concentrated under reduced pressure to yield the conjugate as a yellow oily product (87–88%).

Figure 6:
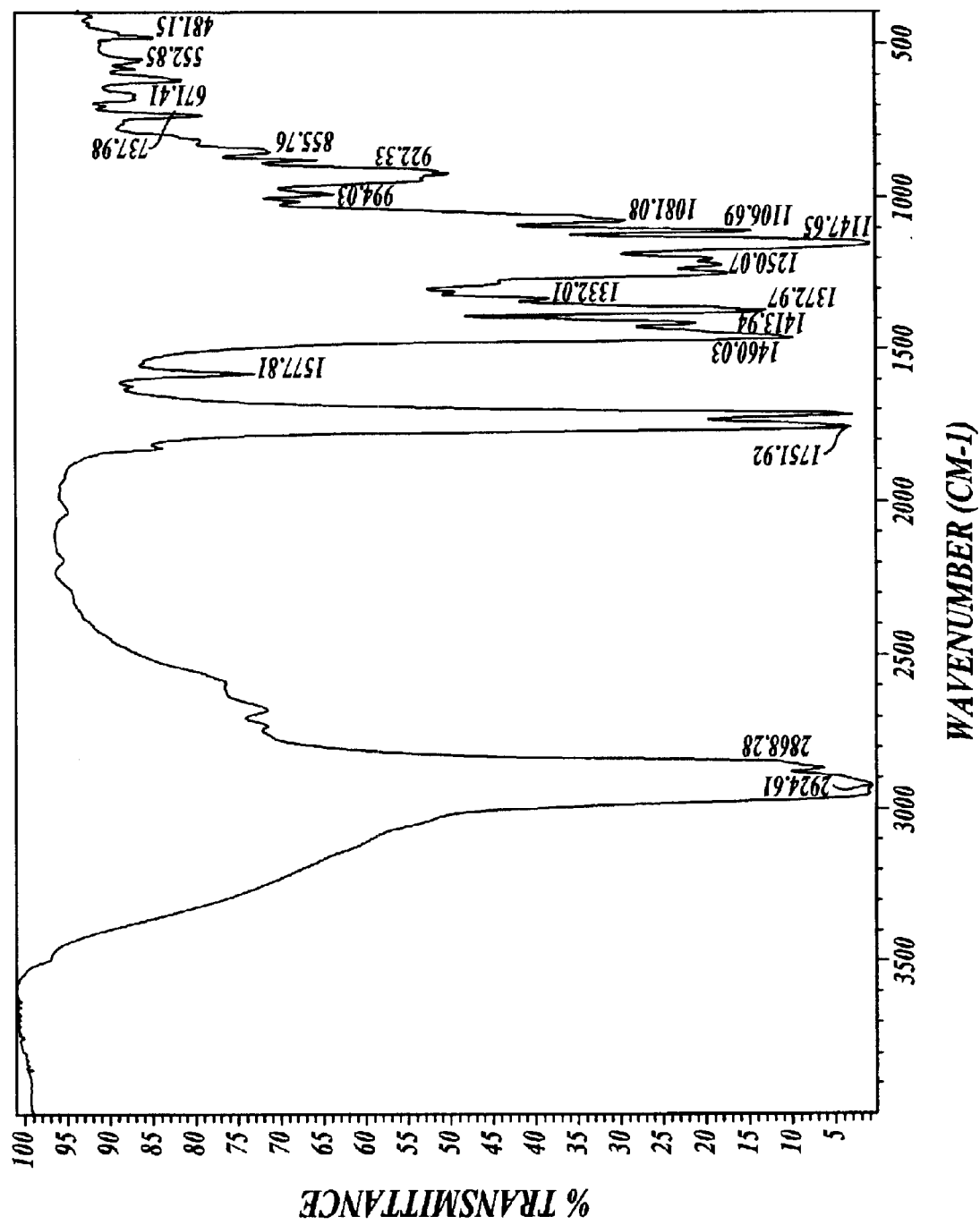
FIG. 6 is the infrared absorbance spectrum of the representative vitamin E pyroglutamate conjugate shown in FIG. 1.

The infrared spectrum of the product is shown in FIG. 6. The conjugate is highly soluble (100 mg/ml) in water, dichloromethane, methanol, acetone, and pentane. An aqueous solution of the conjugate in water (50 mg/ml) has a pH of about 5. The aqueous solution is filterable through a 0.2 micron filter. A 0.1 weight percent solution of the conjugate in water has a surface tension of about 29 dynes/cm (compare with 41 dynes/cm for a 0.1 weight percent aqueous solution of vitamin E succinate polyethylene glycol, TPGS).

Example 2

The Preparation of a Representative Vitamin E Succinic Acid Polyoxyethylene Amine Pyroglutamate Conjugate In this example, the preparation of a representative vitamin E pyroglutamate conjugate is described.

To 1 g of VESA in 100 ml THF was added 1.5 eq. N-methylmorpholine dropwise while stirring and maintaining the temperature at 0° C. with an ice water salt bath. This was followed by dropwise addition of $4.93 \times 10^{-3}$ mole isobutyl chloroformate in THF over a period of 15 minutes while stirring at 0° C. The solution was left stirring for 30 minutes at 0° C., the ice bath removed, and then stirred at room temperature for 30 minutes. After an additional hour of stirring, the solution was filtered using Celite on a glass filter to remove the chloride salt of N-methylmorpholine. The filtrate was then added dropwise to a solution of 4.00 g bispropylamino polyethylene glycol (Sigma) in THF and 1.5 eq. triethylamine in a solution of 10 ml $H_2O$ and 40 ml THF (sonicated until clear) maintained at 0° C. The resulting solution stirred overnight. The following day, the solution was concentrated to dryness to yield an oily product. The product was dissolved in 250 ml dichloromethane and extracted with 3×250 ml 0.1 N HCl, washed with saturated $NaHCO_3$ and 200 ml saturated NaCl solution, and dried over $MgSO_4$. The $MgSO_4$ was filtered with a Whatman #1 filter and the filtrate concentrated to dryness to yield the vitamin E amine product (VESA-PEG-$NH_2$).

Figure 7:
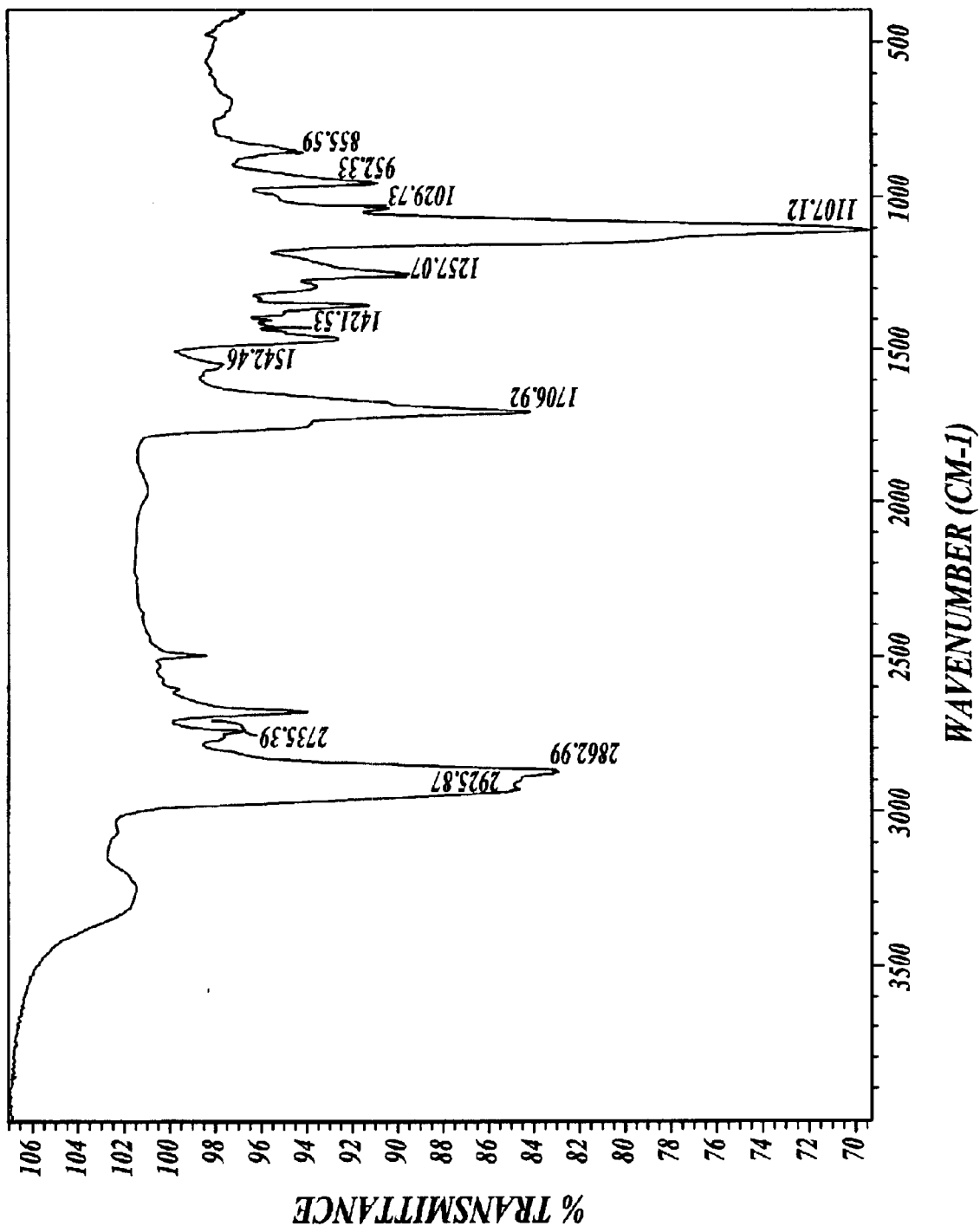
FIG. 7 is the infrared absorbance spectrum of the representative vitamin E pyroglutamate conjugate shown in FIG. 2.

To 1 g (N-benzyloxycarbonyl)pyroglutamic acid in 90 ml THF was added 0.57 g N-methylmorpholine dropwise while stirring and maintaining the temperature at 0° C. with an ice water salt bath. This was followed by dropwise addition of 0.67 g isobutyl chloroformate in THF over a period of 15 minutes while stirring at 0° C. The solution was left stirring for 30 minutes at 0° C., the ice bath removed, and then stirred at room temperature for 30 minutes. After an additional hour of stirring, the solution was filtered using Celite on a glass filter to remove the chloride salt of N-methylmorpholine. The filtrate was then added dropwise to a solution of 4.00 g VESA-PEG-$NH_2$ in THF and 0.577 g triethylamine in a solution of 10 ml $H_2O$ and 40 ml THF (sonicated until clear) maintained at 0° C. The resulting solution stirred overnight. The following day, the solution was concentrated to dryness to yield an oily product. The product was dissolved in 250 ml dichloromethane and extracted with 3×250 ml 0.1 N HCl, washed with saturated $NaHCO_3$ and 200 ml saturated NaCl solution, and dried over $MgSO_4$. The $MgSO_4$ was filtered with a Whatman #1 filter and the filtrate concentrated to dryness to yield an oily product (98%). The infrared spectrum of the product is shown in FIG. 7.

Example 3

The Preparation of a Representative Vitamin E Amine Pyroglutamate Conjugate

In this example, the preparation of a representative vitamin E pyroglutamate conjugate is described.

To 4 g (N-benzyloxycarbonyl)pyroglutamic acid in 150 ml THF was added 2.30 g N-methylmorpholine dropwise while stirring and maintaining the temperature at 0° C. with an ice water salt bath. This was followed by dropwise addition of 2.69 g isobutyl chloroformate in THF over a period of 15 minutes while stirring at 0° C. The solution was left stirring for 30 minutes at 0° C., the ice bath removed from the ice bath and then stirred at room temperature for 30 minutes. After an additional hour of stirring, the solution was filtered using Celite on a glass filter to remove the chloride salt of N-methylmorpholine. The filtrate was then added dropwise to a solution of 6.00 g tocopheramine (Rhodia Chirex) and 2.30 g triethylamine in 60 ml THF maintained at 0° C. The resulting solution was left stirring overnight. The following day, the solution was concentrated to dryness to yield a yellowish-brown, oily product. The product was then dissolved in 250 ml dichloromethane and extracted with 3×250 ml 0.1 N HCl, washed with saturated $NaHCO_3$ and 200 ml saturated NaCl solution, and dried over $MgSO_4$. The $MgSO_4$ was filtered with a Whatman #1 filter. The filtrate was concentrated to dryness to yield a yellow oily product (98%).

Example 4

The Preparation of a Representative Vitamin E Pyrrolidinone Conjugate

In this example, the preparation of a representative vitamin E pyrrolidinone conjugate is described.

To 10 g vitamin E succinic acid (VESA) in 150 ml of dry THF stirred at 0° C. was added dropwise 2.85 g N-methylmorpholine dissolved in 2 ml THF maintained at 0° C. The solution was stirred for several minutes and then followed by dropwise addition of 3.34 g isobutyl chloroformate over a period of 15 minutes while stirring at 0° C. The solution was then left stirring at 0° C. for 30 minutes followed by stirring for another 30 minutes at room temperature. After 1 hour, a fine precipitate settled out (N-methylmorpholine HCl salt) that was filtered on Celite using a glass filter. The filtrate containing VESA-anhydride was placed into a separatory funnel and then added dropwise to 1.92 g 2-pyrrolidinone in 50 ml THF containing 2.85 g of triethylamine at 0° C. The resulting solution was stirred overnight. The following day, the solution was concentrated to dryness to provide a yellow oil. The product was dissolved in 200 ml of dichloromethane and extracted with 200 ml 0.1 N NaOH, washed with 200 ml saturated NaCl solution, and dried over $MgSO_4$. The $MgSO_4$ was filtered with a Whatman #1 filter. The filtrate was concentrated to dryness to yield a yellow, non-viscous oil (87–88%).

Example 5

The Preparation of a Representative Vitamin E Gentisic Acid Conjugate

In this example, the preparation of a representative vitamin E gentisic acid conjugate is described.

Figure 8:
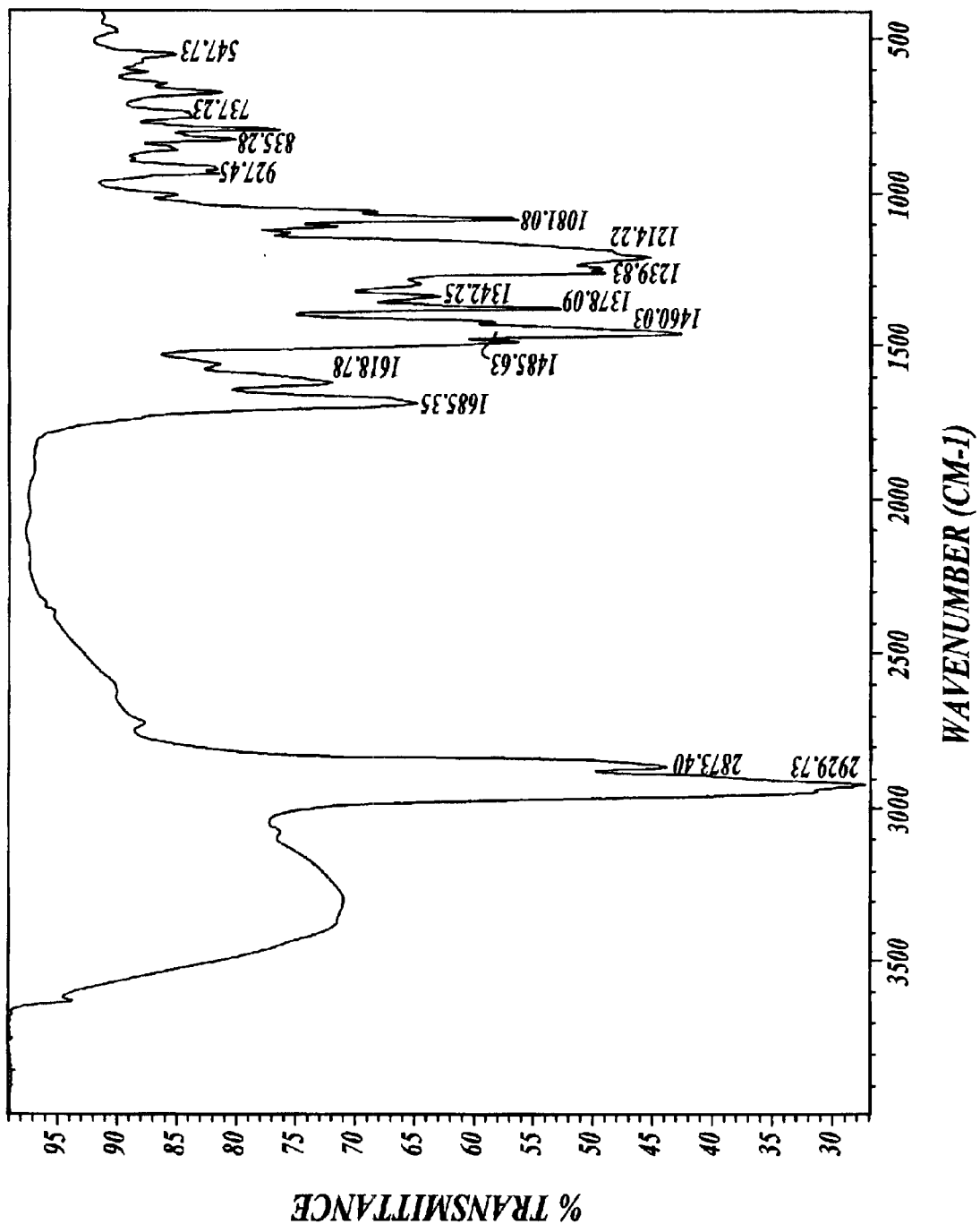
FIG. 8 is the infrared absorbance spectrum of the representative vitamin E gentisic acid conjugate shown in FIG. 5.

To 3.5 g gentisic acid (2,5-dihydroxybenzoic acid) in 200 ml dry THF was added dropwise 4.78 g dicyclohexylcarbodiimide (DCC) in THF. This was followed by dropwise addition of 0.56 g 4-dimethylaminopyridine in THF with rapid stirring at room temperature. The solution was allowed to stir for 10 to 15 minutes and then 10 g vitamin E in THF was added to the mixture. The solution was stirred overnight. The resulting solution was filtered with Celite to remove dicyclohexylurea (DCU). The filtrate was concentrated to dryness to yield a brownish, viscous oil (87–88%). The infrared spectrum of the product is shown in FIG. 8.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound, consisting of a tocopherol moiety covalently coupled to a pyroglutamate moiety through a linker moiety selected from a group consisting of an amine group, a dicarboxylic acid diester group, and a polyoxyethylene group.

2. The compound of claim 1, wherein the linker moiety comprises a succinic acid diester group.

3. The compound of claim 1, wherein the linker moiety comprises a bispropylamino polyoxyethylene group.

4. The compound of claim 1, wherein the pyroglutamate moiety is coupled to the linker through the pyroglutamate amine group.

5. The compound of claim 1, wherein the pyroglutamate moiety is coupled to the linker through the pyroglutamate carboxylic acid group.

6. Tocopherol pyroglutamate.

7. Tocopherol succinate pyroglutamate.

8. Tocopherol succinate bisaminopolyoxyethylene pyroglutamate.

9. Tocopheramine pyroglutamate.

10. A compound, consisting of a tocopherol moiety covalently coupled to a pyrrolidinone moiety through a dicarboxylic acid diester group.

11. The compound of claim 10, wherein the dicarboxylic acid diester group is a succinic acid diester group.

12. Tocopherol pyrrolidinone.

13. Tocopherol succinate pyrrolidinone.

14. A composition, comprising a lipophilic or relatively-water insoluble therapeutic or cosmetic agent and the compound of claim 1.

15. The composition of claim 14, wherein composition is at least one of a solution or emulsion.

16. The composition of claim 14 further comprising a solvent.

17. The composition of claim 14 further comprising a surfactant.

18. A composition, comprising a lipophilic or relatively-water insoluble therapeutic or cosmetic agent and the compound of claim 10.

19. The composition of claim 18, wherein composition is at least one of a solution or emulsion.

20. The composition of claim 18 further comprising a solvent.

21. The composition of claim 18 further comprising a surfactant.

* * * * *

UNITED STATES PATENT AND TRADEMARK OFFICE
CERTIFICATE OF CORRECTION

PATENT NO. : 6,858,227 B1
DATED : February 22, 2005
INVENTOR(S) : M. Lal et al.

It is certified that error appears in the above-identified patent and that said Letters Patent is hereby corrected as shown below:

<u>Title page,</u>
Item [56], References Cited, FOREIGN PATENT DOCUMENTS, delete "WO 0071163 * 11/2000"

<u>Column 10,</u>
Lines 25 and 34, "wherein composition is" should read -- wherein the composition is --

Signed and Sealed this

Twenty-fourth Day of May, 2005

JON W. DUDAS
*Director of the United States Patent and Trademark Office*